(12) United States Patent
Brady et al.

(10) Patent No.: US 7,504,208 B2
(45) Date of Patent: Mar. 17, 2009

(54) SOLID-PHASE FLUORINATION OF URACIL AND CYTOSINE

(75) Inventors: Frank Brady, London (GB); Sajinder Kaur Luthra, London (GB); Edward George Robins, London (GB)

(73) Assignee: Hammersmith Imanet Limited, London (GB)

( * ) Notice: Subject to any disclaimer, the term of this patent is extended or adjusted under 35 U.S.C. 154(b) by 416 days.

(21) Appl. No.: 10/538,904

(22) PCT Filed: Dec. 19, 2003

(86) PCT No.: PCT/GB03/05577

§ 371 (c)(1),
(2), (4) Date: Jun. 14, 2005

(87) PCT Pub. No.: WO2004/056400

PCT Pub. Date: Jul. 8, 2004

(65) Prior Publication Data

US 2006/0120958 A1    Jun. 8, 2006

(30) Foreign Application Priority Data

Dec. 20, 2002    (GB)  ................... 0229683.8

(51) Int. Cl.
C12Q 1/68    (2006.01)
A01N 61/00   (2006.01)
C07G 3/00    (2006.01)
A01N 43/04   (2006.01)

(52) U.S. Cl. .................. 435/6; 514/1; 514/44; 536/4.1
(58) Field of Classification Search ............... 435/6; 536/4.1; 514/1, 44
See application file for complete search history.

(56) References Cited

U.S. PATENT DOCUMENTS 3,808,097 A    4/1974   Fowler
5,312,592 A    5/1994   Andersson

FOREIGN PATENT DOCUMENTS

DE    19951715    3/2001

WO    97/42203    11/1997
WO    03/002157   1/2003

OTHER PUBLICATIONS

Chemical Abstract AN 1988:130967 of J. of Labelled Compounds and Radiopharm. (1987), vol. 24(9), pp. 1029-1042.
Visser—European Journal of Nuclear Medicine (1989) vol. 15, pp. 225-229.
Sutliffe-Goulden J.L., et.al., "Solid phase syntehesis of F-Labelled peptides for positron emission tomography" Bioorganic & Medicinal Chemistry Letters, Oxford, GB, vol. 10, No. 14, Jul. 2000 pp. 1501-1503.
Iwata, R, et.al., "F-Fluoromethyl triflate, a novel and reactive F-fluoromethylating agent: preparation and application to the on-column preparation of F-fluorocholine" Applied Radiation and Isotopes, Pergamon Press Ltd., Exeter, GB., vol. 57, No. 3, tp. 2002 pp. 347-352.
Labroo V.M., et.al., "Direct Electrophilic Fluorination of Tyrosine in Dermorphin Analogues and its effect on Biological Activity Receoptor Affinity and Selectivity" Int'l Journal of Peptide and Protein research, vol. 37, No. 5, 1991, pp. 430-439.
Visser, G.W.M. : "Synthesis and biodistribution of 18F-5-fluorocytosine" Nuclear Medicine Communications, vol. 6, 1985, pp. 455-459.
Ozaki, Shoichiro, et.al.,: "5-fluorouracil derivatives. Part XIX. Preparation containing 5-fluorouracil as a component" Polymer Journal (Tokyo, Japan) (1990), pp. 689-695.
Search Report GB 0229683.8 dated May 29, 2003.
Int'l Search Report PCT/GB2003/005577 dated Jul. 4, 2004.
Int'l preliminary Examination Report for PCT/GB2003/005577 dated Apr. 14, 2005.

*Primary Examiner*—Jezia Riley
(74) *Attorney, Agent, or Firm*—Craig Bohlken

(57) ABSTRACT

The invention relates to a process for the production of an $^{18}$F-labelled tracer which comprises treatment of a solid support-bound precursor of formula (I): SOLID SUPPORT-LINKER-I$^+$-TRACER (I) Y$^-$ wherein the TRACER is of formula (A): or an amine protected derivative thereof, wherein Y$^-$ is an anion, preferably trifluoromethylsulphonate (triflate) anion; and R$^1$ is either (i) a group CH—NP$^{1,4}$P$^{2,4}$ in which P$^{1,4}$ and P$^{2,4}$ are each independently hydrogen or a protecting group, or (ii) a carbonyl group; with $^{18}$F$^-$ to produce the labelled tracer of formula (II) or an amine protected derivative thereof, wherein R$^1$ is as defined for the compound of formula (I).

8 Claims, No Drawings

SOLID-PHASE FLUORINATION OF URACIL AND CYTOSINE

This application is a filing under 35 U.S.C. 371 of international application number PCT/GB2003/005577, filed Dec. 19, 2003, which claims priority to application number 0229683.8 filed Dec. 20, 2002, in Great Britain the entire disclosure of which is hereby incorporated by reference.

The present invention relates to novel processes for the production of radiolabelled tracers, in particular for the production of $^{18}$F-labelled compounds such as 5[$^{18}$F]fluorouracil and 5[$^{18}$F]fluorocytosine which may be suitable for use as Positron Emission Tomography (PET) radiotracers. The invention also comprises radiopharmaceutical kits using these novel processes.

The favoured radioisotope for PET, $^{18}$F, has a relatively short half-life of 110 minutes. $^{18}$F-labelled tracers for PET therefore have to be synthesised and purified as rapidly as possible, and ideally within one hour of clinical use. Standard synthetic methods for introducing fluorine-18 are relatively slow and require post-reaction purification (for example, by HPLC) which means that it is difficult to obtain the $^{18}$F-labelled tracer for clinical use in good radiochemical yield. There is also a need for automation to protect the operator from radiation exposure. Many radiofluorinations are complicated procedures and it is necessary to simplify them to facilitate automation.

The present invention provides solution- and solid-phase processes for producing $^{18}$F-labelled tracers quickly and with high specific activity yet avoiding time-consuming purification steps, such that the resultant $^{18}$F-labelled tracer is suitable for use in PET. The solid-phase methods particularly also lend themselves to automation with advantages of ease of production and greater throughput. The invention also comprises radiopharmaceutical kits which use such processes and thus provide the radiopharmacist or clinician with a convenient means of preparing an $^{18}$F-labelled tracer.

Solid-phase nucleophilic fluorination methods are described in co-pending International Patent Application PCT/GB02/02505.

According to a first aspect, the invention provides a process for the production of an $^{18}$F-labelled tracer which comprises treatment of a solid support-bound precursor of formula (I):

$$\text{SOLID SUPPORT-LINKER-I}^+\text{-TRACER} \quad \text{Y}^- \tag{I}$$

wherein the TRACER is of formula (A):

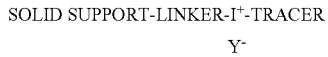

(A)

or an amine protected derivative thereof, wherein Y is an anion, preferably trifluoromethylsulphonate (triflate) anion; and R$^1$ is either (i) a group CH—NP$^{1A}$P$^{2A}$ in which P$^{1A}$ and P$^{2A}$ are each independently hydrogen or a protecting group, or
(ii) a carbonyl group;

with $^{18}$F$^-$ to produce the labelled tracer of formula (II)

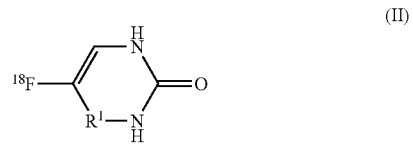

(II)

or an amine protected derivative thereof, wherein R$^1$ is as defined for the compound of formula (I);

optionally followed by:
(i) removal of excess $^{18}$F$^-$, for example by ion-exchange chromatography; and/or
(ii) removal of any protecting groups; and/or
(iii) removal of organic solvent, and/or
(iv) formulation of the resultant compound of formula (II) as an aqueous solution.

The compound of formula (I) may be conveniently prepared from a functionalised commercially available resin such as a Merrifield Resin or Wang Resin. Suitably, a hydroxylodoaryl (such as an iodophenol) containing LINKER group is treated with an inorganic base, such as cesium carbonate and then added to the resin, pre-swollen with an inert solvent, such as N,N-dimethylformamide and allowed to react at elevated temperature, for example 30 to 80° C. Excess reagents may be removed by washing the resin with further inert solvent. The resultant iodophenol functionalised resin may then be treated with a source of acetate anions (such as actetic acid, acetic anhydride, or acetyl chloride) in the presence of an oxidising agent, such as hydrogen peroxide to provide the corresponding diacetoxy-iodophenyl functionalised resin. The diacetoxy-iodophenyl functionalised resin may then be stirred in an inert solvent, such as dichloromethane, in the presence of acid such as hydrochloric acid, trifluoromethane sulphonic acid, or acetic acid at a low temperature, suitably −40° C. to 10° C. before addition of the tracer, suitably functionalised as a boronic acid or triorgano tin (suitably trialkyl tin) derivative which may be coupled to the resin at a non-extreme temperature. As in previous steps, the desired compound of formula (I) may be separated by filtration and washing with an inert solvent.

As the $^{18}$F-labelled tracer of formula (II) is removed from the solid-phase into solution, all unreacted precursor remains bound to the resin and can be separated by simple filtration, thus obviating the need for complicated purification, for example by HPLC. The $^{18}$F-labelled tracer of formula (II) may be cleaned up by removal of excess A, for example by ion-exchange chromatography and/or by removal of any organic solvent. The resultant $^{18}$F-labelled tracer of formula (II) may then be further made-up into an aqueous formulation for clinical use.

In the compounds of formulae (I) and in the following more specific aspects of the invention, the "SOLID SUPPORT" may be any suitable solid-phase support which is insoluble in any solvents to be used in the process but to which the LINKER and/or TRACER can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compounds of formulae (I) and in the following more specific aspects of the invention, the "LINKER" may be any suitable organic group which serves to space the reactive site sufficiently from the solid support structure so as to maximise reactivity. Suitably, the LINKER comprises zero to four aryl groups (suitably phenyl) and/or a $C_{1-16}$alkyl (suitably $C_{1-6}$alkyl) or $C_{1-16}$haloalkyl (suitably $C_{1-6}$haloalkyl), typically $C_{1-16}$ fluoroalkyl (suitably $C_{1-6}$ fluoroalkyl), or $C_{1-16}$alkoxy or $C_{1-16}$haloalkoxy (suitably $C_{1-6}$alkoxy or $C_{1-6}$haloalkoxy) typically $C_{1-16}$fluoroalkoxy (suitably $C_{1-6}$fluoroalkoxy), and optionally one to four additional functional groups such as amide or sulphonamide groups. Examples of such linkers are well known to those skilled in the art of solid-phase chemistry, but include:

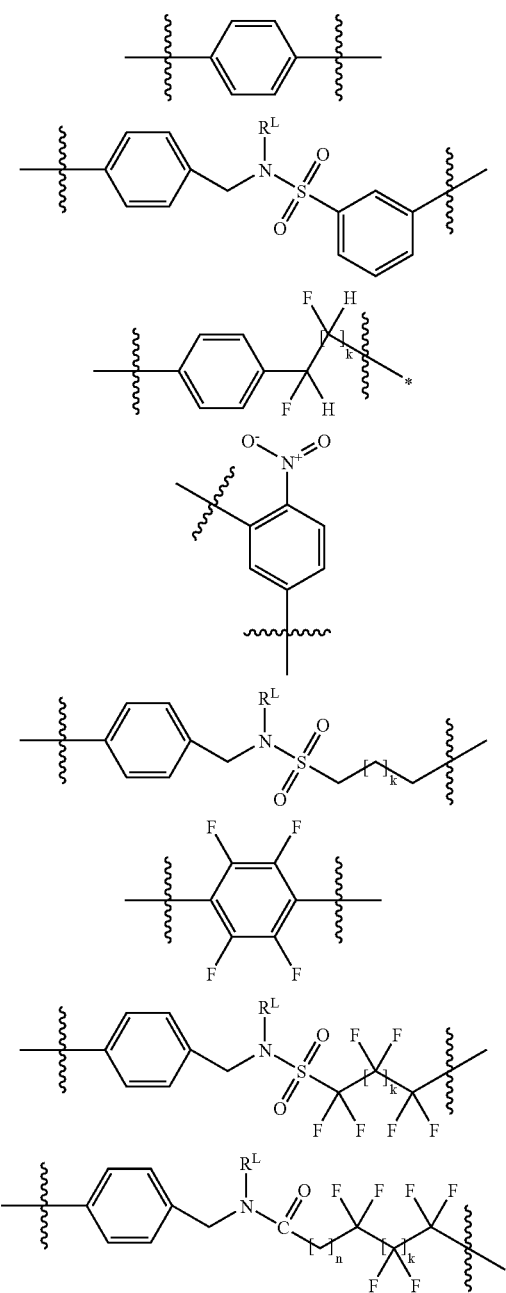

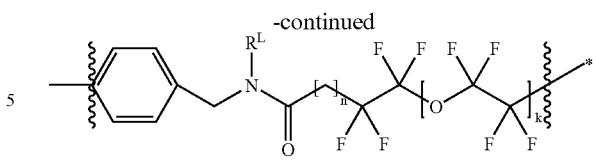

wherein at each occurrence, k is an integer of 0 to 3, n is an integer of 1 to 16, and $R^L$ is hydrogen or $C_1$—alkyl.

In the compound of formula (I) and in the following more specific aspects of the invention, the LINKER is as defined above but suitably comprises an aryl group (suitably phenyl) adjacent to the $I^+$. Preferred examples include

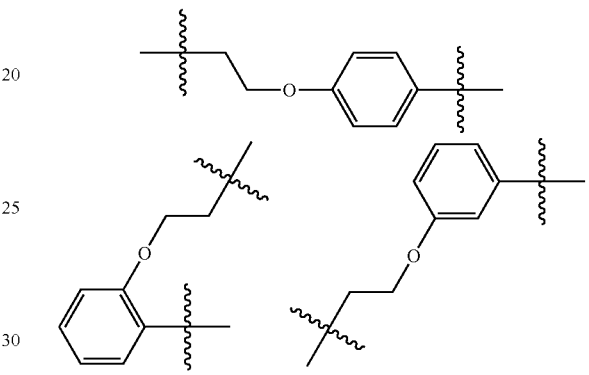

The present invention provides in a further aspect, a process for the production of 5[$^{18}$F]fluorouracil which comprises treatment of a solid support-bound precursor of formula (Ia):

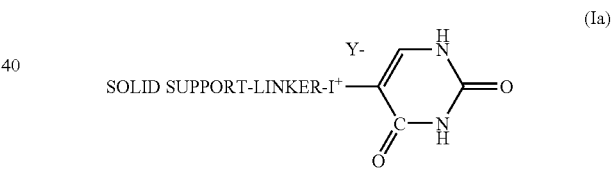

or an amine protected derivative thereof, wherein $Y^-$ is an anion, preferably trifluoromethylsulphonate (triflate) anion; with $^{18}F^-$ to produce the labelled tracer of formula (IIa)

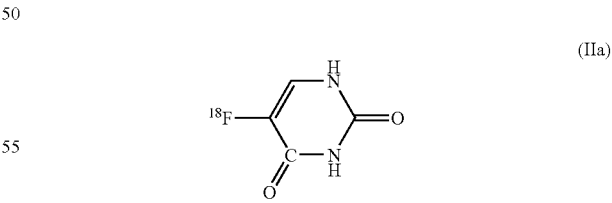

or an amine protected derivative thereof, optionally followed by:
(i) removal of excess $^{18}F^-$, for example by ion-exchange chromatography; and/or
(ii) removal of organic solvent; and/or
(iii) removal of any protecting groups; and/or
(iv) formulation of the resultant compound of formula (IIa) as an aqueous solution.

The present invention provides in a further aspect, a process for the production of 5[$^{18}$F]fluorocytosine which comprises treatment of a solid support-bound precursor of formula (Ib):

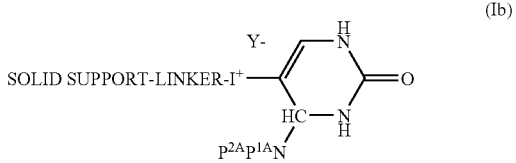

or an amine protected derivative thereof, wherein Y$^-$ is an anion, preferably trifluoromethylsulphonate (triflate) anion, P$^{1A}$ and P$^{2A}$ are independently hydrogen or a protecting group;
with $^{18}$F$^-$ to produce the labelled tracer of formula (IIb)

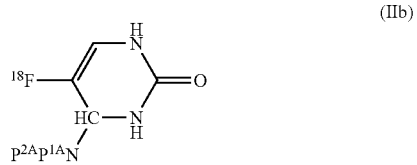

or an amine protected derivative thereof, wherein P$^{1A}$ and P$^{2A}$ are as defined for the compound of formula (Ib), optionally followed by:
(i) removal of excess $^{18}$F$^-$, for example by ion-exchange chromatography; and/or
(ii) removal of organic solvent; and/or
(iii) removal of any protecting groups; and/or
(iv) formulation of the resultant compound of formula (IIb) as an aqueous solution.

As would be apparent to the person skilled in the art, it may be necessary to protect functional groups in the TRACER to avoid unwanted reactions during the radiolabelling process. Such protection may be achieved using standard methods of protecting group chemistry. After the radiolabelling is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc. For example, the amine functionality in the compound of formula (I) may be protected by esters, suitably C$_{1-6}$alkyl or C$_{1-6}$haloalkyl esters, preferably acyl esters such as t-butoxycarbonyl, or ethers, preferably C$_{1-6}$alkyl ethers, or as amides suitably C$_{1-6}$alkylamides such as formyl amide. These protecting groups may be conveniently removed by hydrolysis, for example in the presence of acid or base. Such deprotection may be effected using a solid supported acid or base catalysts that render the need for post deprotection neutralisation unnecessary.

Treatment of the compound of formula (I), (Ia), or (Ib) with $^{18}$F$^-$ may be effected by treatment with any suitable source of $^{18}$F, such as Na$^{18}$F, K$^{18}$F, Cs$^{18}$F, tetraalkylammonium $^{18}$F$^-$ fluoride, or tetraalkylphosphonium $^{18}$F$^-$ fluoride. To increase the reactivity of the fluoride, a phase transfer catalyst such as 4,7,13,16,21,24 hexaoxa-1,10-diazabicyclo[8,8,8]hexacosane may be added and the reaction performed in a non protic solvent. These conditions give reactive fluoride ions.

The treatment with $^{18}$F$^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a non-extreme temperature, for example, 15° C. to 180° C., preferably at elevated temperature. On completion of the reaction, the $^{18}$F-labelled tracer of formula (II) dissolved in the solvent is conveniently separated from the solid-phase by filtration. The same fluorination techniques may be used in the other aspects of the invention.

Any excess $^{18}$F$^-$ may be removed from the solution of $^{18}$F-tracer by any suitable means, for example by ion-exchange chromatography or solid phase absorbents. Suitable ion-exchange resins include BIO-RAD AG 1-X8 or Waters QMA and suitable solid phase absorbents include alumina. The excess $^{18}$F$^-$ may be removed using such solid phases at room temperature in aprotic solvents.

Any organic solvent may be removed by any standard method such as by evaporation at elevated temperature in vacuo or by passing a stream of inert gas such as nitrogen or argon over the solution.

Before use of the $^{18}$F-labelled tracer, it may be appropriate to formulate it, for example as an aqueous solution by dissolving the $^{18}$F-labelled tracer in sterile isotonic saline which may contain up to 10% of a suitable organic solvent such as ethanol, or a suitable buffered solution such as phosphate buffer. Other additives may be added such as ascorbic acid to reduce radiolysis.

The compounds of formula (I) are novel and thus form a further aspect of the present invention. Thus, for example, compounds of formula (Ia) and formula (Ib) also form separate aspects of the present invention.

As described above, the advantages of such solid-phase processes for preparation of $^{18}$F-labelled tracers include the relative speed of the process, simplified purification methods and ease of automation—all of which mean that the processes are suitable for preparation of $^{18}$F-labelled tracers for use in PET. Accordingly, the present invention provides a process according to the invention for the production of a $^{18}$F-labelled tracer of formula (II), (IIa), or (IIb) for use in PET.

In an alternative aspect of the invention, the compounds of formula (II), (IIa), and (IIb) can also be prepared by analogous solution phase methods. Accordingly, there is provided a process for the production of an $^{18}$F-labelled tracer which comprises treatment of a compound of formula (III), (IIIa), or (IIIb):

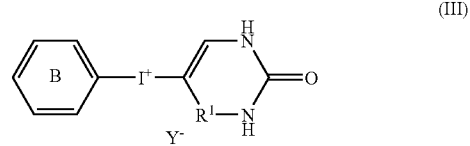

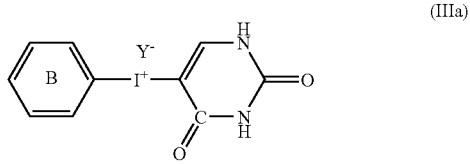

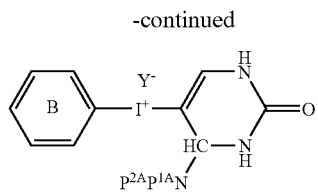

(IIIb)

or an amine protected derivative thereof, wherein $R^1$, $P^{2A}$, $P^{1A}$, and $Y^-$ are as defined in formula (I), and phenyl ring B is optionally substituted with one to five substituents independently selected from halo, $C_{1-6}$alkyl, $C_{1-6}$haloalkyl, hydroxy, $C_{1-6}$alkoxy, amino, $C_{1-6}$hydroxyalkyl, and nitro;

with $^{18}F^-$ to produce the labelled tracer of formula (II), (IIa), or (IIb) respectively as defined above or an amine protected derivative thereof, optionally followed by:

(i) removal of excess $^{18}F^-$, for example by ion-exchange chromatography; and/or
(ii) removal of any protecting groups; and/or
(iii) removal of organic solvent; and/or
(iv) formulation of the resultant compound of formula (II), (IIa), or (IIb) as an aqueous solution.

Conveniently, the solid support bound precursor of formula (I) or a compound of formula (III), (IIIa), or (IIIb) or an amine protected derivative thereof, could be provided as part of a kit to a radiopharmacy. The kit may contain a cartridge which can be plugged into a suitably adapted automated synthesiser. The cartridge may contain, apart from the precursor compound, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers is requirements for radioactive concentration, volumes, time of delivery etc.

Conveniently, all components of the kit are disposable to minimise the possibilities of contamination between runs and may be sterile and quality assured.

The invention further provides a radiopharmaceutical kit for the preparation of an $^{18}F$-labelled tracer for use in PET, which comprises:

(i) a vessel containing a compound of formula (I), (Ia), (Ib), (III), (IIa), or (IIIb) or an amine protected derivative thereof; and
(ii) means for eluting the vessel with a source of $^{18}F^-$;
(iii) an ion-exchange cartridge for removal of excess $^{18}F^-$; and optionally
(iv) a cartridge for solid-phase deprotection of the resultant product of formula (II), (IIa), or (IIb).

The invention further provides a cartridge for a radiopharmaceutical kit for the preparation of an $^{18}F$-labelled tracer for use in PET which comprises:

(i) a vessel containing a compound of formula (I), (Ia), (Ib), (III), (IIIa), or (IIIb) or an amine protected derivative thereof; and
(ii) means for eluting the vessel with a source of $^{18}F^-$.

In a further aspect of the invention, there is provided a method for obtaining a diagnostic PET image which comprises the step of using a radiopharmaceutical kit or a cartridge for a radiopharmaceutical kit as described above.

The invention will now be illustrated by way of the following Examples. Throughout the Examples, abbreviations used are as follows:

DMF: N,N-dimethylformamide
w/v: weight/volume
h: hour(s)
tlc: thin layer chromatography
THF: tetrahydrofuran
eq.: equivalents

EXAMPLES

Example 1

Synthesis of 5[$^{18}F$]-fluorouracil

Example 1(i)

Synthesis of PS iodo-phenyl benzyl ether

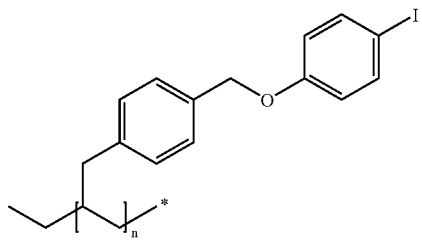

To a suspension of Wang Resin pre-swollen in DMF (2 ml) a solution of cesium carbonate and Iodophenol in DMF were added. The mixture was stirred for 3 h at 60° C. and then left at room temperature overnight. After filtration the resin was washed consecutively with methanol, dichloromethane, DMF and THF before thorough drying under high vacuum.

Example 1(ii)

Synthesis of PS diacetoxy-iodo-phenyl benzyl ether

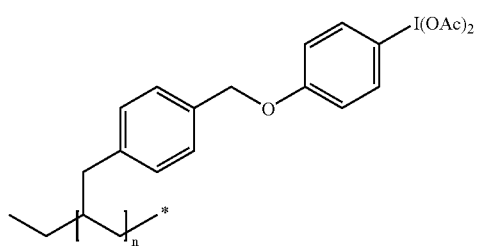

A suspension of the resin above was treated with acetic anhydride and hydrogen peroxide (see method of S. Ficht, Tetrahedron, 57 (2001) 4863) in a 4:1 ratio at 40° C. overnight. The resin was then filtered and washed thoroughly with methanol and then-dried under high vacuum until dry.

Example 1(iii)

Synthesis of Solid-support Bound Precursor for 5[$^{18}$F]-fluorouracil

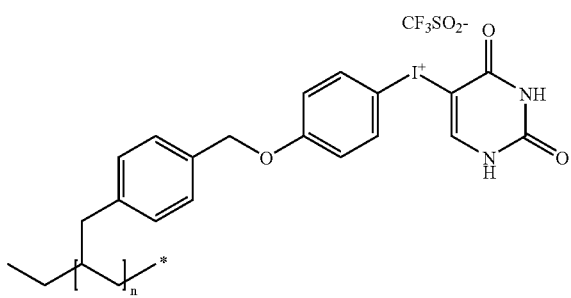

To a suspension of the resin from Example 1(ii) above in dichloromethane, trifluoromethane sulfonic acid is added dropwise at a temperature of −30° C. for 15 minutes. The mixture is then warmed to 0° C. for a further 15 minutes before being stirred at room temperature overnight. The suspension is then cooled to −30° C. and 5-dihydroxyboranyl-1H-pyrimidine-2,4-dione (Schinazi et al, Tetrahedron Lett.; 1978, 4981) is added, and the suspension is stirred for 1 h before warming to room temperature and further stirring overnight The mixture is then filtered and washed thoroughly with dichloromethane and diethyl ether before drying under vacuum.

Example 1(iv)

Radiofluorination to Prepare 5[$^{18}$F]-fluorouracil

To a portion of the resin from Example 1(iii) held in a cartridge is added a solution in dry acetonitrile of kryptofix, potassium carbonate and [$^{18}$F]-fluoride. The suspension is heated to 85° C. for 10 minutes and then the solution is filtered off. The resin is washed with acetonitrile (1 ml) and all the contents collected together before evaporation of the solvent prior to formulation.

Example 2

Synthesis of Polymer Supported 5-uracil iodonium salt

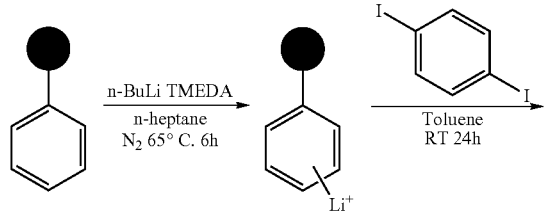

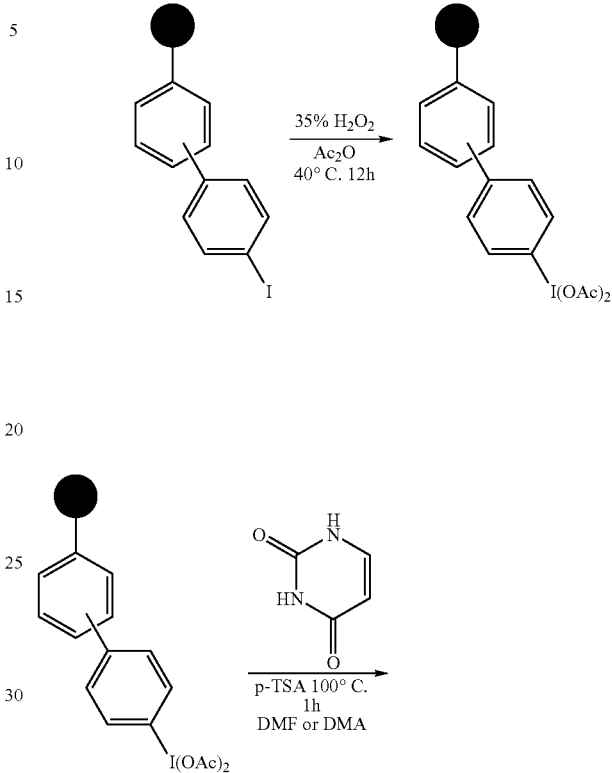

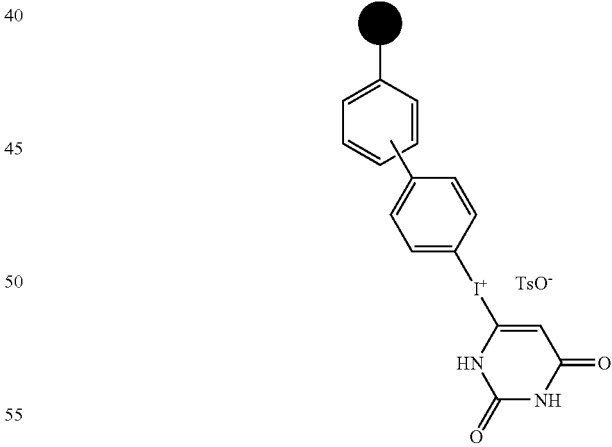

Example 2(i)

Lithiation of poly(styrene)

Reference J. Org. Chem, 1976, 41, 3877

Under an inert atmosphere, 2.8 g of 2% cross-linked poly (styrene) (I) was suspended in 20-25 mL n-heptane containing 25 mmol TMEDA (tetramethyl ethylenediamine) and 33.75 mmol butyl lithium. The reaction mixture was stirred rapidly and warmed to 60-65° C. for ca. 5 hours during which time the reaction mixture became a deep orange colour. The mixture was then cooled to ambient temperature and the supernatant decanted. The remaining orange residue was washed with n-hepatane (2×20 mL) and dried under vacuum.

Example 2(ii)

Preparation of iodophenyl terminated poly(styrene)

Reference Polymer 2000, 41, 4005

The lithiatedpoly(styrene) (prepared as described in Example 2(i)) was treated with dry toluene (20 mL) and 5.6 mmol of 1,4-diiodobenzne and the mixture stirred 3 is 5 under an inert atmosphere for ca. 48 hours. The resulting yellow/orange mixture was filtered and the solid residue washed with 20 mL portions of diethyl ether, water, methanol and hexanes. The resulting yellow solid was dried at 60° C. under vacuum for 2 hours yielding a pale yellow, free-flowing solid.

Isolated yield: 3.205 g (ca. 82%) Elemental Anlaysis: % I 13.02 corresponding to an Iodine loading of 1.03 mmol/g.

Example 2(iii)

Oxidation of iodophenyl terminated poly(styrene) to Corresponding iododiacetate Reference Synth. Commun. 2001, 31, 111

To a flask containing 30 mL of acetic anhydride at 40° C. was slowly added 7.5 mL of a 35% solution of hydrogen peroxide with stirring. The mixture was kept at 40° C. (no higher than 45° C.) for a further 4 hours before 0.875 g of polymer (prepared as described in Example 2(ii)) was added portion-wise and the mixture stirred for 12 hours at 40° C. The resulting very pale yellow reaction mixture was cooled to ambient temperature and the polymer isolated by filtration. The title polymer was washed with consecutive 10 mL portions of methanol, water and diethyl ether before being dried under vacuum in the absence of light.

Isolated yield: 0.66 g Analysis by FT-IR and comparison to literature.

Example 2(iv)

Polymer Supported 5-uracil iodonium salt

Reference: Chem. Heterocyclic Compounds 1973, 4, 510

Synthesis of polymer bound uracil derivative was attempted by analogy with the solution phase chemistry reported.

To a suspension 0.50 g of polymer supported iodosodiacetate (prepared as described in Example 2(iii)) in 8 mL of DMF was added 0.55 mmol of PTSA (para-toluene sulfonic acid) and the mixture heated with rapid stirring to 100° C. The mixture became a bright yellow colour on addition of the acid and once at 100° C., 0.55 mmol of uracil was added and the mixture stirred for a further 1 hour. The resulting yellow mixture was cooled to ambient temperature and water added to precipitate the polymer and the title product was isolated by filtration.

Isolated yield 0.35 g. Product polymer showed broad bands by IR spectroscopy in the region 1800-1400 $cm^{-1}$ consistent with those reported for the molecular phenyl derivative. Stepwise analysis of products from PS-I(OAc)$_2$ to PS-I(OH)OTs to PS-I(Uracil)OTs shows the disappearance of CO band on addition of PTSA in the region 1760-1680 $cm^{-1}$ and re-appearance of broad bands in this region after reaction with uracil.

The polymer supported 5-uracil iodonium salt so obtained may be radiofluorinated using methods analogous to those described in Example 1(iv).

Model Example 3

Synthesis of N,N-diacetyl-5-iodouracil

To a 250 mL flask was added 5-iodouracil (3.5 g, 14.7 mmol) and anhydrous 1,4-dioxane (25 mL) and the mixture cooled in an ice-bath. Triethylamine, freshly distilled from KOH under $N_2$, (4.3 mL, 30.9 mmol) was added to the flask and the reaction mixture stirred rapidly for 5 minutes before acetyl chloride (3.24 mL, 45.6 mmol) was very slowly added to the mixture. The resulting mixture was stirred at ambient temperature overnight. Removal of solvent and volatiles under vacuum afforded an orange/yellow residue. The residue was treated with $H_2O$ (100 mL) and extracted using benzene (4×50 mL). The benzene extracts were combined and dried over anhydrous $Na_2SO_4$. After filtration and removal of solvent under vacuum, the crude yellow residue was purified by column chromatography using hexane:ethylacetate (3:1) yielding 2.74 g (58%) of N,N-diacetyl-5-iodouracil as a white solid.

TLC (Hexane:EtOAc 3:1) R$_f$0.26. $^1$H-NMR (CDCl$_3$) δ 8.64 (s, 1H, vinyl H), 2.75 (s, 3H, N-1-acetyl-CH$_3$), 2.59 (s, 3H, N-3-acetyl-CH$_3$).

This chemistry may be used by analogy to prepare amine protected uracil or cytosine iodonium salt derivatives for use in radiofluorination reactions as described above.

What is claimed is:

1. A process for the production of an $^{18}$F-labeled tracer which comprises treatment of a solid support-bound precursor of formula (I):

SOLID SUPPORT-LINKER-I$^+$-TRACER    (I)

Y$^-$ wherein the TRACER is of formula (A):

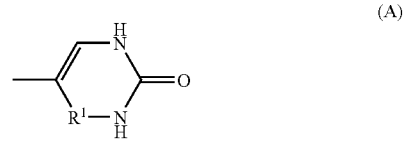

wherein Y⁻ is an anion, preferably trifluoromethylsulphonate (triflate) anion; and R¹ is either (i) a group CH—NP^{1A}P^{2A} in which P^{1A} and P^{2A} are each independently hydrogen or a protecting group, or (ii) a carbonyl group;

with ¹⁸F to produce the labelled tracer of formula (II)

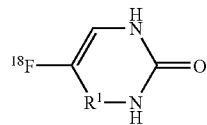
(II)

wherein R¹ is as defined for the compound of formula (I): optionally followed by:
(i) removal of excess ¹⁸F⁻, by ion-exchange chromatography; and/or
(ii) removal of any protecting groups; and/or
(iii) removal of organic solvent; and/or
(iv) formulation of the resultant compound of formula (II) as an aqueous solution.

2. A process according to claim 1 for the production of 5[¹⁸F]fluorouracil which comprises treatment of a solid support-bound precursor of formula (Ia):

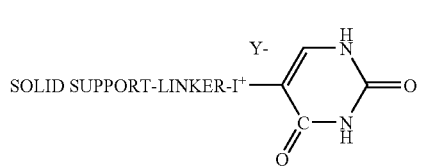
(Ia)

wherein Y⁻ is an anion, preferably trifluoromethylsulphonate (triflate) anion:

with ¹⁸F to produce the labelled tracer of formula (IIa)

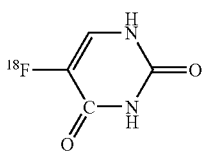
(IIa)

optionally followed by:
(i) removal of excess ¹⁸F⁻, by ion-exchange chromatography; and/or
(ii) removal of organic solvent; and/or
(iii) removal of any protecting groups; and/or
(iv) formulation of the resultant compound of formula (IIa) as an aqueous solution.

3. A process for the production of a ¹⁸F-labelled tracer of formula (II), according to claim 1, for use in PET which comprises treatment of a solid support-bound precursor of formula (I):

SOLID SUPPORT-LINKER-I⁺-TRACER
Y⁻
(I)

wherein the TRACER is of formula (A):

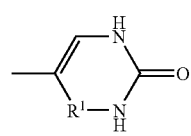
(A)

wherein Y⁻ is an anion, preferably trifluoromethylsulphonate (triflate) anion; and R¹ is either (i) a group CH—NP^{1A}P^{2A} in which P^{1A} and P^{2A} are each independently hydrogen or a protecting group, or (ii) a carbonyl group;

wherein R¹ is as defined for the compound of formula (I);

optionally followed by:
(i) removal of excess ¹⁸F⁻, by ion-exchange chromatography; and/or
(ii) removal of any protecting groups; and/or
(iii) removal of organic solvent; and/or
(iv) formulation of the resultant compound of formula (II) as an aqueous solution.

4. A compound of formula (I):

SOLID SUPPORT-LINKER-I⁺-TRACER
Y⁻
(I)

wherein the TRACER is of formula (A):

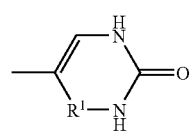
(A)

wherein Y⁻ is an anion, preferably trifluoromethylsulphonate (triflate) anion; and R¹ is either (i) a group CH—NP^{1A}P^{2A} in which P^{1A} and P^{2A} are each independently hydrogen or a protecting group, or (ii) a carbonyl group.

5. A compound of formula (Ia):

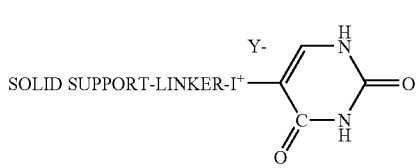
(Ia)

wherein Y⁻ is an anion, preferably trifluoromethylsulphonate (triflate) anion.

6. A radiopharmaceutical kit for the preparation of an ¹⁸F-labelled tracer for use in PET, which comprises treatment of a solid support-bound precursor of formula (I):

SOLID SUPPORT-LINKER-I⁺-TRACER    (I)
                Y⁻ wherein the TRACER is of formula (A):

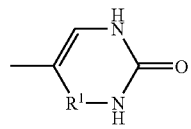    (A)

wherein Y⁻ is an anion, preferably trifluoromethylsulphonate (triflate) anion; and
R¹ is either (i) a group CH—NP$^{1A}$P$^{2A}$ in which P$^{1A}$ and P$^{2A}$ are each independently hydrogen or a protecting group, or (ii) a carbonyl group;
wherein R¹ is as defined for the compound of formula (I);
which comprises:
(i) a vessel containing a compound of formula (I) and
(ii) means for eluting the vessel with a source of $^{18}$F⁻;
(iii) an ion-exchange cartridge for removal of excess $^{18}$F⁻; and optionally
(iv) a cartridge for solid-phase deprotection of the resultant product of formula (II), claim 1.

7. A cartridge for a radiopharmaceutical kit for the preparation of an $^{18}$F-labelled tracer for use in PET which comprises treatment of a solid support-bound precursor of formula (I):

SOLID SUPPORT-LINKER-I⁺-TRACER    (I)
                Y⁻ wherein the TRACER is of formula (A):

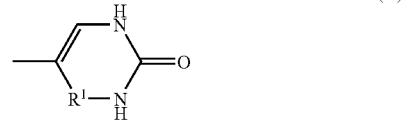    (A)

wherein Y⁻ is an anion, preferably trifluoromethylsulphonate (triflate) anion; and
R¹ is either (i) a group CH—NP$^{1A}$P$^{2A}$ in which P$^{1A}$ and P$^{2A}$ are each independently hydrogen or a protecting group, or (ii) a carbonyl group:
wherein R¹ is as defined for the compound of formula (I);
further wherein
(i) a vessel containing a compound of formula (I), as defined in claim 1 -and
(ii) means for eluting the vessel with a source of $^{18}$F⁻.

8. A method for obtaining a diagnostic PET image which comprises the step of using a cartridge for a radiopharmaceutical kit according to claim 7.

\* \* \* \* \*